(12) United States Patent
Genest et al.

(10) Patent No.: US 10,314,674 B2
(45) Date of Patent: Jun. 11, 2019

(54) DENTAL PROSTHETICS MANIPULATION, SELECTION, AND PLANNING

(75) Inventors: Dominic Genest, Quebec (CA); David Giasson, Quebec (CA)

(73) Assignee: Nobel Biocare Canada Inc., Quebec (CA)

(*) Notice: Subject to any disclaimer, the term of this patent is extended or adjusted under 35 U.S.C. 154(b) by 1752 days.

(21) Appl. No.: 12/703,601

(22) Filed: Feb. 10, 2010

(65) Prior Publication Data
US 2011/0196654 A1 Aug. 11, 2011

(51) Int. Cl.
*A61C 5/77* (2017.01)
*A61C 13/00* (2006.01)

(52) U.S. Cl.
CPC .................. *A61C 13/0004* (2013.01)

(58) Field of Classification Search
CPC ................................................ A61C 13/0004
USPC ........................................ 703/1; 700/98, 118
See application file for complete search history.

(56) References Cited

U.S. PATENT DOCUMENTS

| | | | |
|---|---|---|---|
| 5,273,429 A | 12/1993 | Nappi et al. | |
| 5,674,069 A | 10/1997 | Osorio | |
| 6,231,342 B1 | 5/2001 | Osorio et al. | |
| 6,506,054 B2 | 1/2003 | Shoher et al. | |
| 6,648,640 B2* | 11/2003 | Rubbert et al. | 433/24 |
| 6,846,179 B2 | 1/2005 | Chapouland et al. | |
| 6,915,178 B2 | 7/2005 | O'Brien et al. | |
| 6,957,118 B2 | 10/2005 | Kopelman et al. | |
| 7,013,191 B2* | 3/2006 | Rubbert et al. | 700/98 |
| 7,029,275 B2* | 4/2006 | Rubbert et al. | 433/24 |
| 7,092,780 B2 | 8/2006 | Ganley et al. | |
| 7,110,844 B2 | 9/2006 | Kopelman et al. | |
| 7,134,874 B2 | 11/2006 | Chishti et al. | |
| 7,140,877 B2 | 11/2006 | Kaza | |
| 7,156,655 B2* | 1/2007 | Sachdeva et al. | 433/24 |
| 7,228,191 B2 | 6/2007 | Hofmeister et al. | |
| 7,236,842 B2 | 6/2007 | Kopelman et al. | |
| 7,333,874 B2 | 2/2008 | Taub et al. | |
| 7,383,094 B2 | 6/2008 | Kopelman et al. | |
| 7,590,462 B2* | 9/2009 | Rubbert et al. | 700/98 |
| 7,717,708 B2* | 5/2010 | Sachdeva et al. | 433/24 |
| 8,021,147 B2* | 9/2011 | Sporbert et al. | 433/24 |
| 8,121,718 B2* | 2/2012 | Rubbert et al. | 700/98 |

(Continued)

FOREIGN PATENT DOCUMENTS

EP 0 756 852 2/1997

OTHER PUBLICATIONS

Cardeli and Pike, Squeak: a Language for Communicating with Mice, Jul. 22-26, 1985, San Francisco, ACM SIGGRAPH, vol. 19, No. 3, pp. 199-204.*

*Primary Examiner* — Juan C Ochoa
(74) *Attorney, Agent, or Firm* — Knobbe Martens Olson & Bear LLP

(57) ABSTRACT

Presented herein are methods, systems, devices, and computer-readable media for dental prosthetics manipulation, selection, and planning. Embodiments include an overlapped, or semi-realistic 3D rendering, a localized abstraction of the dental plan, and/or a globalized abstraction of the dental plan. Various selection, manipulation, and planning functions are available for the displays. A dentist or other operator can use the various portions of the display to interact with, manipulate, and plan a dental prosthetic. In some embodiments, tools are also provided, such as a full crown manipulation.

17 Claims, 15 Drawing Sheets

(56) References Cited

U.S. PATENT DOCUMENTS

| | | |
|---|---|---|
| 8,177,551 B2 * | 5/2012 | Sachdeva et al. ............... 433/2 |
| 2001/0021498 A1 | 9/2001 | Osorio et al. |
| 2002/0110786 A1 | 8/2002 | Dillier |
| 2004/0185422 A1 | 9/2004 | Orth et al. |
| 2004/0265770 A1 | 12/2004 | Chapoulaud et al. |
| 2006/0008776 A1 | 1/2006 | Orth et al. |
| 2006/0040236 A1 | 2/2006 | Schmitt |
| 2006/0105294 A1 | 5/2006 | Burger et al. |
| 2006/0275736 A1 * | 12/2006 | Wen et al. .................... 433/213 |
| 2007/0015111 A1 | 1/2007 | Kopelman et al. |
| 2008/0015727 A1 | 1/2008 | Dunne et al. |
| 2008/0220395 A1 | 9/2008 | Marshall et al. |
| 2008/0261165 A1 | 10/2008 | Steingart et al. |
| 2009/0248184 A1 * | 10/2009 | Steingart et al. ............... 700/98 |
| 2009/0325128 A1 * | 12/2009 | Holzner et al. ............ 433/201.1 |
| 2011/0224955 A1 * | 9/2011 | Fisker et al. ..................... 703/1 |

\* cited by examiner

DENTAL PROSTHETICS MANIPULATION, SELECTION, AND PLANNING

BACKGROUND

Field

The present application generally relates to dental planning, and more particularly to user interfaces and associated technology for case designing in dental prosthetics.

Description of Related Technology

The use of computer systems to design dental prosthetics has increased in recent years. The computer systems allow a dentist, dental technician, or other operator to design dental prosthetics for individual patients. These individual prosthetic designs are often called "situations," "dental plans," or "prosthetic plans." Operators using the computer systems can design plans based on a library of the teeth shapes and positions, patient data, and available equipment and hardware. For example, an operator may have at her disposal 3D models built based on scans of gums, bones, implants, dental models, etc. The patient's anatomy can define aspects of the dental plan. For example, desired symmetry with other teeth and antagonistic teeth help define the functional and aesthetic aspects of the dental plan. Based on these data, the operator may make a custom dental plan for the patient. All of this is typically done using a mouse and a two-dimensional computer interface.

A problem with the approach described above is that it may be difficult to manipulate the inputs to the dental planning software (such as the patient-specific data) and the various aspects of the dental plan. Together, all of the inputs to the dental planner, including the patient-specific data, combined with all the aspects of the desired dental plan might be called the "dental data." In order to visualize the relative placements, all of the various aspects of the dental data would be rendered in a manner that collocates them on the computer screen such that they overlap on the visual display. The overlapped nature of the interface makes it very difficult to select and/or manipulate the various aspects of the dental data.

There are also problems with the individual manipulation of the various aspects of dental data. For example, when working on a bridge, it is important that the buccal cusps of the teeth on the bridge are aligned. Manipulating various pontics, or units, that make up the bridge when manipulating the shape, position, and size of the units may cause, among other problems, misalignment of the buccal cusps.

These problems and others are addressed by the systems, methods, and devices and computer-readable media described herein.

SUMMARY

Presented herein are methods, systems, devices, and computer-readable media for dental prosthetics manipulation, selection, and planning. This summary in no way limits the invention herein, but instead is provided to summarize a few of the embodiments.

Embodiments herein include systems and methods for dental prosthetics manipulation, selection, and planning. The techniques may include receiving, from an operator via a computer system, dental data related to a desired dental plan. This dental data may include patient-specific input data as well as aspects of the desired dental plan (such as a bridge or crown). The operator of the system may then be presented with an overlapped electronic representation of two or more aspects of the dental data and a non-overlapped abstract electronic representation of the two or more aspects of the dental data. There may then be received at the computer system, relative to the abstract electronic representation, an indication of an operation to be performed regarding one or more aspects of the two or more aspects of the dental data and the operation indicated by the operator may be presented in the overlapped electronic representation. In various embodiments, the indicated operation may be selection, deselection, make transparent, make invisible, etc. The operation may also indicate multiple tooth positions.

In various embodiments, the dental data may include a dental plan for one or more tooth positions; the non-overlapped abstract electronic representation of the one or more aspects of the dental data may include a single globalized unit representation of the one or more tooth positions; and presenting the operation indicated, in the overlapped electronic representation may include presenting the operation indication in the overlapped electronic representation for each of the one or more tooth positions. The desired data may also include a dental plan for two or more teeth; the non-overlapped abstract electronic representation of the one or more aspects of the dental data may include a localized abstract electronic representation of each tooth in the plan; and presenting, in the overlapped electronic representation, an operation indicated for a particular tooth in the localized abstract electronic representation may include presenting the operation indication in the overlapped electronic representation for only the particular tooth.

In some embodiments, the system, methods, and computer readable media may also include: presenting to the operator a second abstract representation of the two or more aspects of the dental data; receiving, relative to the second abstract electronic representation, a second indication of an operation to be performed regarding one or more aspects of the two or more aspects of the dental data; and presenting, in the overlapped representation, the second operation indicated.

In some embodiments, information about dental data related to a desired dental plan is received from an operator via a computer system. Also received is an indication to add a bridge to the desired data. Then a user interface to allow the bridge to be manipulated as a whole is presented. A computer system may manipulate the underlying data representation of the bridge based on commands from the operator using the user interface. The system may also present to the operator, using the computer system, the desired data, including the manipulated bridge using the underlying data representation.

In yet other embodiments, information about dental data related to a desired dental plan is received from an operator via a computer system. The operator of the computer system is presented with a first electronic representation of two or more aspects of the desired data and a second electronic representation of the two or more aspects of the dental data. Received at the computer system, relative to the second electronic representation, may be an indication of an operation to be performed regarding one or more aspects of the two or more aspects of the dental data. The operation indicated may then be presented, in the first electronic representation.

Numerous other embodiments are described throughout herein.

For purposes of summarizing the invention and the advantages achieved over the prior art, certain objects and advantages of the invention are described herein. Of course, it is to be understood that not necessarily all such objects or advantages need to be achieved in accordance with any particular embodiment. Thus, for example, those skilled in the art will recognize that the invention may be embodied or carried out in a manner that achieves or optimizes one advantage or group of advantages as taught or suggested herein without necessarily achieving other objects or advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

DETAILED DESCRIPTION OF SPECIFIC EMBODIMENTS

Overview

Figure 1:
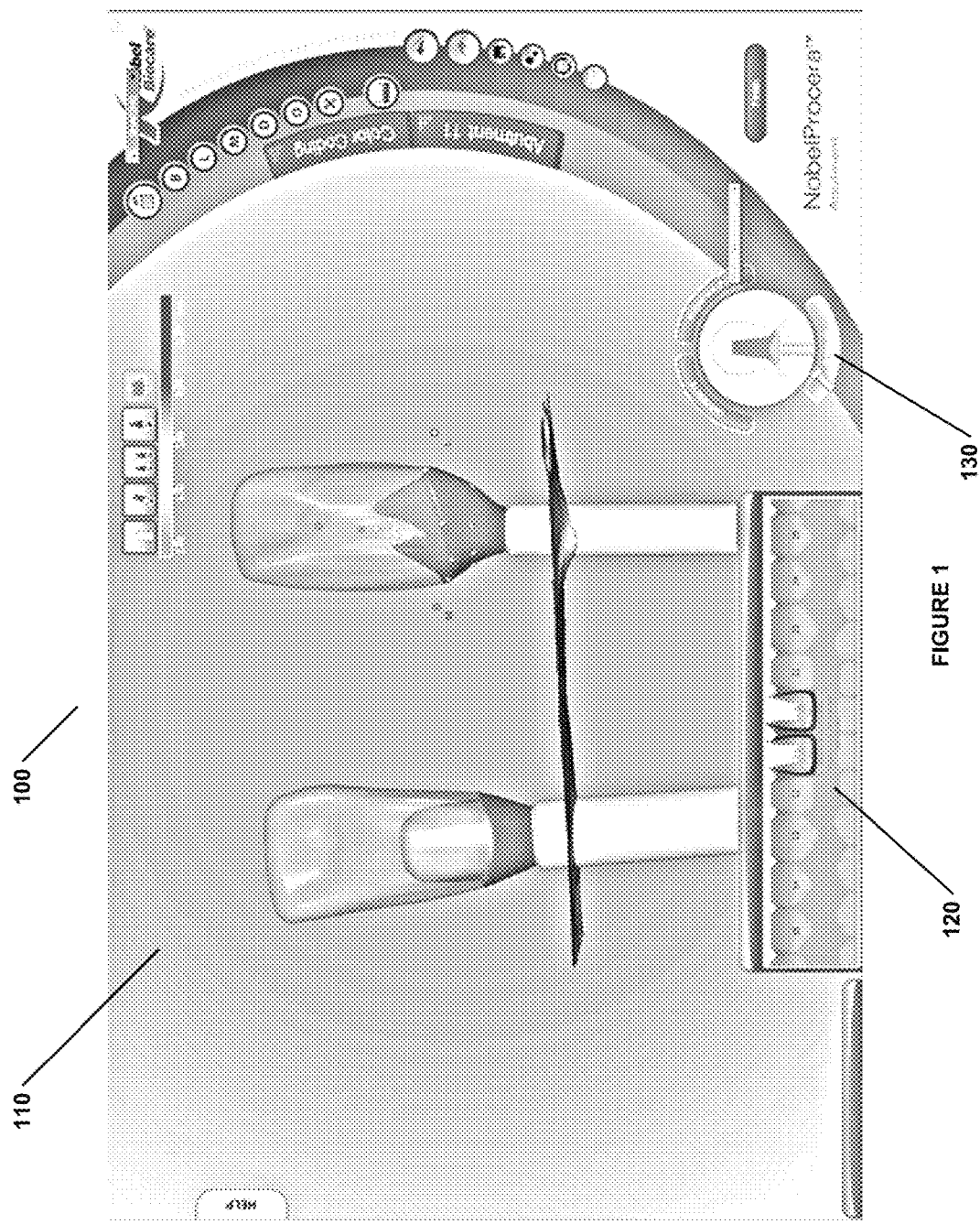
FIG. 1 illustrates a first display for dental prosthetics, manipulation, selection, and planning.

Three-dimensional ("3D") or computer-aided design ("CAD") software can be used for dental prosthetic design. An operator can plan the dental prosthetic by building up and manipulating various aspects of the dental plan in the 3D or CAD software. The input data for such systems may include models made based on 3D scans of patient-specific anatomy, prosthetics, and/or hardware. The input data and models could also include standard or default prosthetics, hardware, or library of teeth, any of which can be manually or automatically adapted to the patient's anatomy. The operator may plan a framework, such as a bridge or crown framework, or, in some embodiments, a full anatomic bridge, crown, etc. In preparation for making or modifying a dental plan, an operator may load in models of the existing teeth, gums, and a wax-up of a prosthesis or abutment that is to be refined and then optionally upload a library of teeth as guidance for building the bridge. As noted above, all of the input data, such as the patient's anatomical data, combined with the data related to the dental plan may be termed the "dental data." As such, when the "aspects" of the dental data are discussed, those aspects may be related to the patient's anatomical data (such as scanned gums, teeth, etc); prosthetic hardware that has been added to the dental plan; teeth, crowns, etc. that have been added to the dental plan; and other displayable data relating to the input data or the dental plan, including library teeth.

Based on the input data, the operator may be able to refine and manipulate the dental plan. For example, if the dental planning includes implant placement, then the operator may be able to modify the alignment of the implant associated with an abutment. If the dental planning includes the design or modification of an abutment, then the operator may be able to manipulate the orientation and shape of the abutment, including making the abutment parallel to another abutment. The operator may be able to color or shade code the images displayed in order to learn about clearance, thickness, and other properties of the plan, and see if thicknesses or clearances are outside of desired ranges. The operator may also be able to manipulate the crown associated with the abutment.

In some embodiments, the operator may be able to match up scans of two or more impressions of the patient's teeth, prepare those impressions, including orienting impressions and culling unneeded parts of the 3D models. The operator may also be able to define bridge insertion axes, and be able to scale, orient, refine, and deform bridges and crowns. The computer system may allow the operator to define margin and preparation lines for teeth to allow for the joinder of high and low resolution models as well as manipulations for other aspects of the dental data. The operator may be able to do global crown placement as well as individual crown placement to match the desired anatomy, symmetry, or aesthetics. Specifically regarding bridges, the operator may be able to resize a bridge in a dental plan, change its orientation, scale, and placement as a whole, thereby preserving the relative alignment of the buccal cusps. The operator may also be able to manipulate individual pontics or units on the bridge, notwithstanding that this may make it more difficult to align the buccal cusps. Numerous other possible manipulations, preparations, and other operations will be known to those skilled in the art.

As noted herein, manipulating dental data can be difficult when the data is displayed in an overlapping or semi-realistic manner. This is, in part, because, in an overlapped or 3D display, multiple portions of the data are projected onto the same 2D plane, the screen. Therefore, when interacting with the models of the various components of the dental data via the 2D screen, it can be difficult to determine with which part of the dental data the operator intends to interact. Consider the portion 110 of display 100 in FIG. 1. In that portion, two crowns are visible, semi-transparently, over abutments. If an operator attempts to select or manipulate either the abutment or the crown where the two overlap in the display, then the computer will have to choose one or the other component to select or manipulate, and that choice may not comport with the operator's desire.

Various embodiments herein can overcome some of these problems by providing the operator with multiple options for the selecting and manipulating the dental data. The localized abstraction portion will allow the operator to select individual aspects of the dental data or dental plan and perform operations on that individual aspect (such as making it transparent, invisible, etc.). The globalized abstraction portion may allow the operator to globally select, e.g., over one or more tooth positions, like aspects of the dental data for multiple tooth positions. The overlapped portion may show a semi-realistic or rendered 3D version of the dental data, including the dental plan, and may allow selection of those things that are visible in the dental plan.

By using the localized abstraction portion of the display, the operator may be able to select or manipulate individual aspects of the dental data. For example, the operator may be able to select a single abutment and then make all of the other aspects in the multi-unit dental plan invisible. This may be possible even if the single abutment were not previously visible in overlapped portion—because its abstraction may still be visible in the localized abstraction portion of the display. Also, if the abutment were obscured by some other aspect of the dental data in the overlapped view (e.g., a crown), then the operator may not be able to select the abutment in the overlapped view, because the crown is "in the way." The operator would still be able to select the abutment in the localized abstraction, because the localized abstract portion may show the abutment in a cross-sectional or other non-overlapped arrangement (and allow for selection) regardless of relative display positions in the overlapped portion of the display.

By using the globalized abstraction portion of the display, the operator may be able to select or manipulate multiple, like aspects of the dental data all at once. If there were multiple units in a dental plan for a bridge, and an operator was trying to make all of the underlying teeth, and only the teeth, visible, this could take quite a while in the overlapped portion of the display. The operator might have to first make all of the aspects of the dental data visible and then, tooth position by tooth position, select and make invisible all aspects of the dental data "above" the teeth (e.g., the copings). By using an embodiment where there is a globalized abstraction portion, the operator may be able to either globally make invisible all of the copings, etc. in the dental plan (by selecting and making invisible the single crown in the globalized portion of the display) or by selecting the globalized abstraction of the tooth and hitting a Hide Others button.

Embodiments herein are not limited to the overlapped portion 110, localized abstraction portion 120, and globalized abstraction portion 130. Various displays may include fewer than these three portions or may include other portions. For example, if there were a mixed dental plan with one or more of each of abutments and bridges being designed, then there may be, for example, two globalized abstraction portions, one of which is globalized abstraction of the abutment data and another of which is a globalized abstraction of bridge data. The portions of the display 100 may allow for more natural and intuitive selection, manipulation, and planning by allowing the dentist to select various portions of the dental data in either a local or global manner. Embodiments of a display may also include many other selection and manipulation functions, such as hiding everything except the selected component. These and other embodiments are described in detail herein.

Exemplary System

Figure 2:
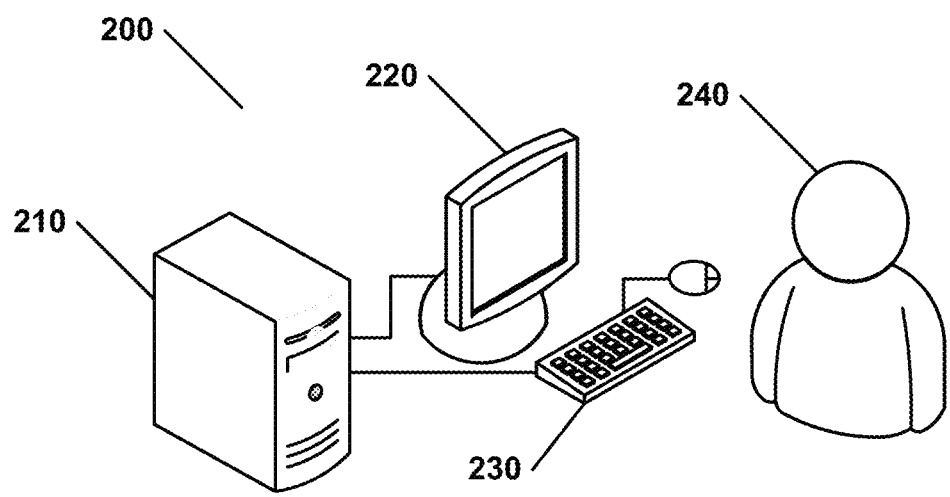
FIG. 2 illustrates an exemplary system for dental implant manipulation, selection, and planning.

FIG. 2 illustrates an exemplary system 200 for dental planning. The system 200 may include one or more computers 210 coupled to one or more displays 220, and one or more input devices 230. An operator 240, who may be a dentist, dental technician, or other person, may plan dental prosthetics using system 200 by manipulating the one or more input devices 230, which may be a keyboard and/or a mouse. In some embodiments, while working on the dental plan, the operator 240 may view the dental plan and other related dental data on the display 220. The display 220 may include two or more display regions or portions, each of which displays a different view of the dental data. For example, in some embodiments, the display 220 may show a semi-realistic rendering of the dental data, an expanded localized abstraction of the dental data, and/or a globalized abstraction of the dental data. Each of these displays may be linked internally within a program and data on computer 210. For example, a program running on a computer 210 may have a single internal representation of the dental data in memory and the internal representation may be displayed in two or more abstract or semi-realistic manners on display 220.

In some embodiments, the operator 240 may be able to perform a command, such as select, or make transparent, opaque, or invisible, on a particular substructure in the dental data. The operator 240 may be able to perform this command by manipulating the input device 230, such as clicking with a mouse on a particular region of one of the abstract or semi-realistic versions of the dental data displayed on the display 220. For example, an operator 240 may click the mouse on a crown for a tooth in order to select that crown. An operator 240 might also click the mouse on the abutment in the globalized abstraction portion in order to make visible all of the planned abutments for all of the teeth to be restored. Additionally, a dental technician 240 might, in certain embodiments, be able to select just the abutment of a particular tooth in the localized portion of the display in order that only that abutment is visible. Then, the overlapped portion might show only that abutment and make invisible the rest of the overlapping portions of the plan for that and other teeth. Numerous examples and embodiments of possible operations are discussed herein.

In various embodiments, the computer 210 may include one or more processors, one or more memories, and one or more communication mechanisms. In some embodiments, more than one computer may be used to execute the modules, methods, and processes discussed herein. Additionally, the modules and processes herein may each run on one or multiple processors, on one or more computers; or the modules herein may run on dedicated hardware. The input devices 230 may include one or more keyboards (one-handed or two-handed), mice, touch screens, voice commands and associated hardware, gesture recognition, or any other means of providing communication between the operator 240 and the computer 210. The display 220 may be a 2D or 3D display and may be based on any technology, such as LCD, CRT, plasma, projection, et cetera.

The communication among the various components of system 200 may be accomplished via any appropriate coupling, including USB, VGA cables, coaxial cables, FireWire, serial cables, parallel cables, SCSI cables, IDE cables, SATA cables, wireless based on 802.11 or Bluetooth, or any other wired or wireless connection(s). One or more of the components in system 200 may also be combined into a single unit or module. In some embodiments, all of the electronic components of system 200 are included in a single physical unit or module.

Process Overview

Figure 3:
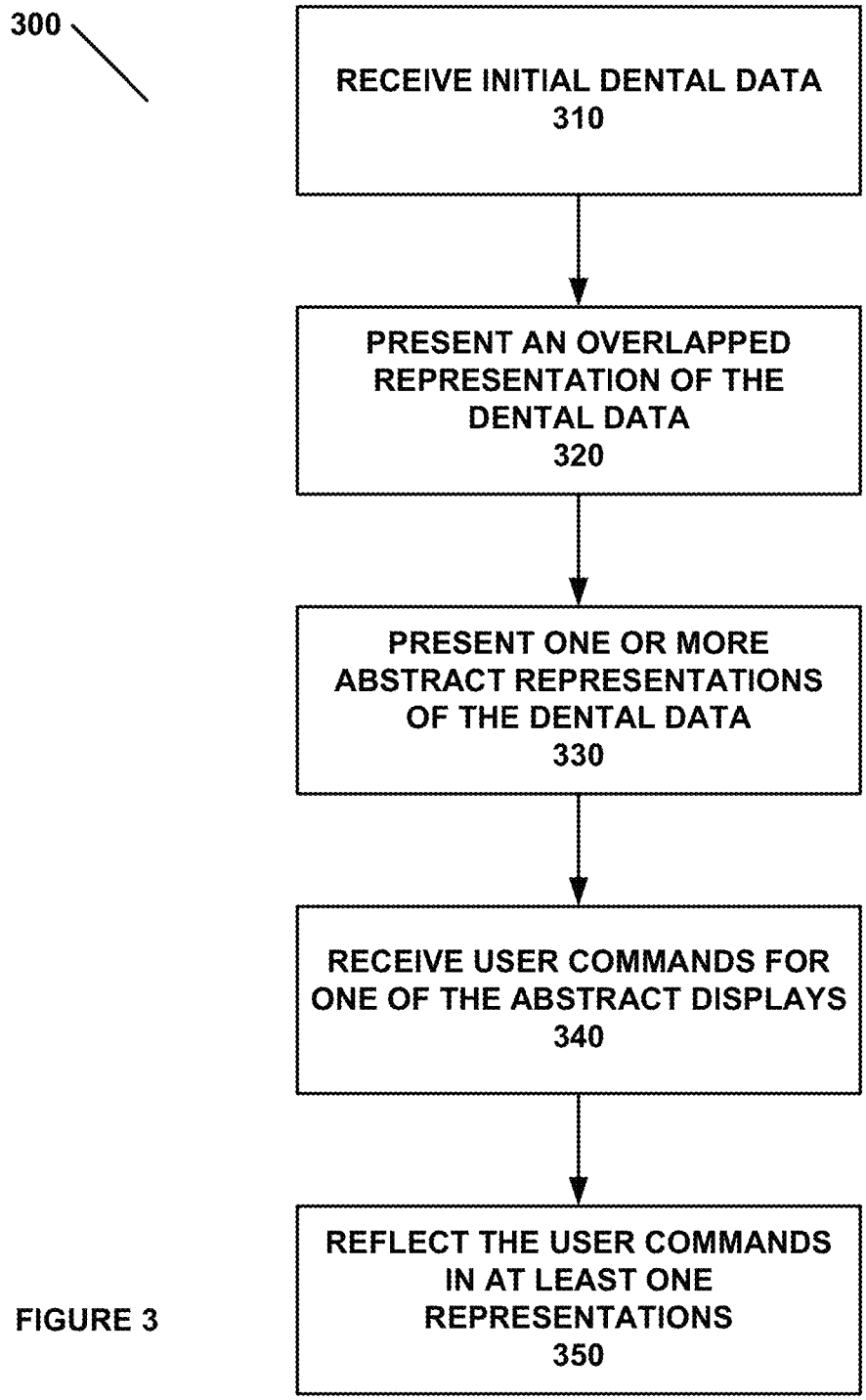
FIG. 3 illustrates a method for dental prosthetics manipulation, selection, and planning.
Figure 4:
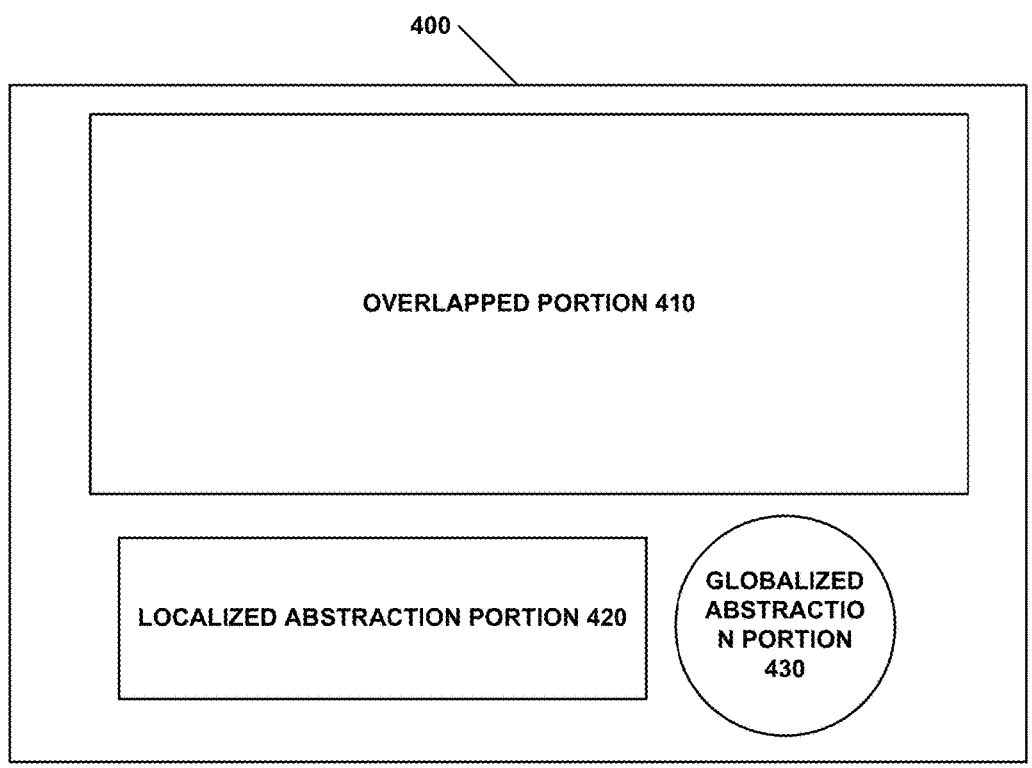
FIG. 4 illustrates a second display for dental prosthetics, manipulation, selection, and planning.

FIG. 3 illustrates a method 300 for dental prosthetics manipulation, selection, and planning. FIG. 4 illustrates a second display for dental prosthetics, manipulation, selection, and planning. The description of method 300 will be described with respect to the exemplary display of FIG. 4. The method 300 is not, however, limited to just the display of FIG. 4 and may be associated with other displays, including others described herein. In some embodiments, the method 300 may run on a computer 210 and cause display on display 230 of FIG. 2. The method 300 may also run on one or more other systems and display on one or more displays.

In step 310, the initial dental data is received. The initial dental data received can include patient-specific data, such as scans of bones, gums, wax-ups, etc. The initial dental data may also include elements of a proposed dental plan. This initial dental data may be received in a number of different ways. For example, it may be loaded from a file or memory. The dental data may also have been made in another program. For example, it may have been constructed, including scanning in the various necessary bones, gums, wax-ups, etc. in the system of U.S. patent application Ser. No. 12/703,596, entitled Dental Data Planning, filed concurrently herewith, the contents of which are hereby incorporated by reference in their entirety for all purposes. Alternatively, the dental data may be developed using the system described herein or in any other appropriate manner.

In various embodiments, the initial dental data can also be manipulated in various ways. The manipulation may include indicating a finish line to indicate where the prosthesis should start (e.g., for a tooth-supported bridge). Based on the finish line, the system may also automatically generate the coping or the bridge. Other manipulations of the dental plan may include defining an abutment, coping, implant, etc. Various embodiments of this are discussed throughout herein. These manipulations may take place as part of steps 310, 340, and/or 350, or separately from those steps.

After the initial dental data is received, then, in step 320, an overlapped representation of the dental data is displayed in a first display, such as the semi-realistic or overlapped portion 410 of FIG. 4. In some embodiments, the overlapped portion may include a 3D rendering of the dental data. The overlapped portion may show certain components of the dental data as being opaque and transparent (or various levels of transparency). Further, in some embodiments, the overlapped portion may exclude certain components of the dental plan. Consider, for example, FIG. 5, which illustrates a third display 500 for dental prosthetics, manipulation, selection, and planning. In that depicted example, a bridge is visible and opaque and a bite index is transparent in the overlapped portion 510.

Figure 5:
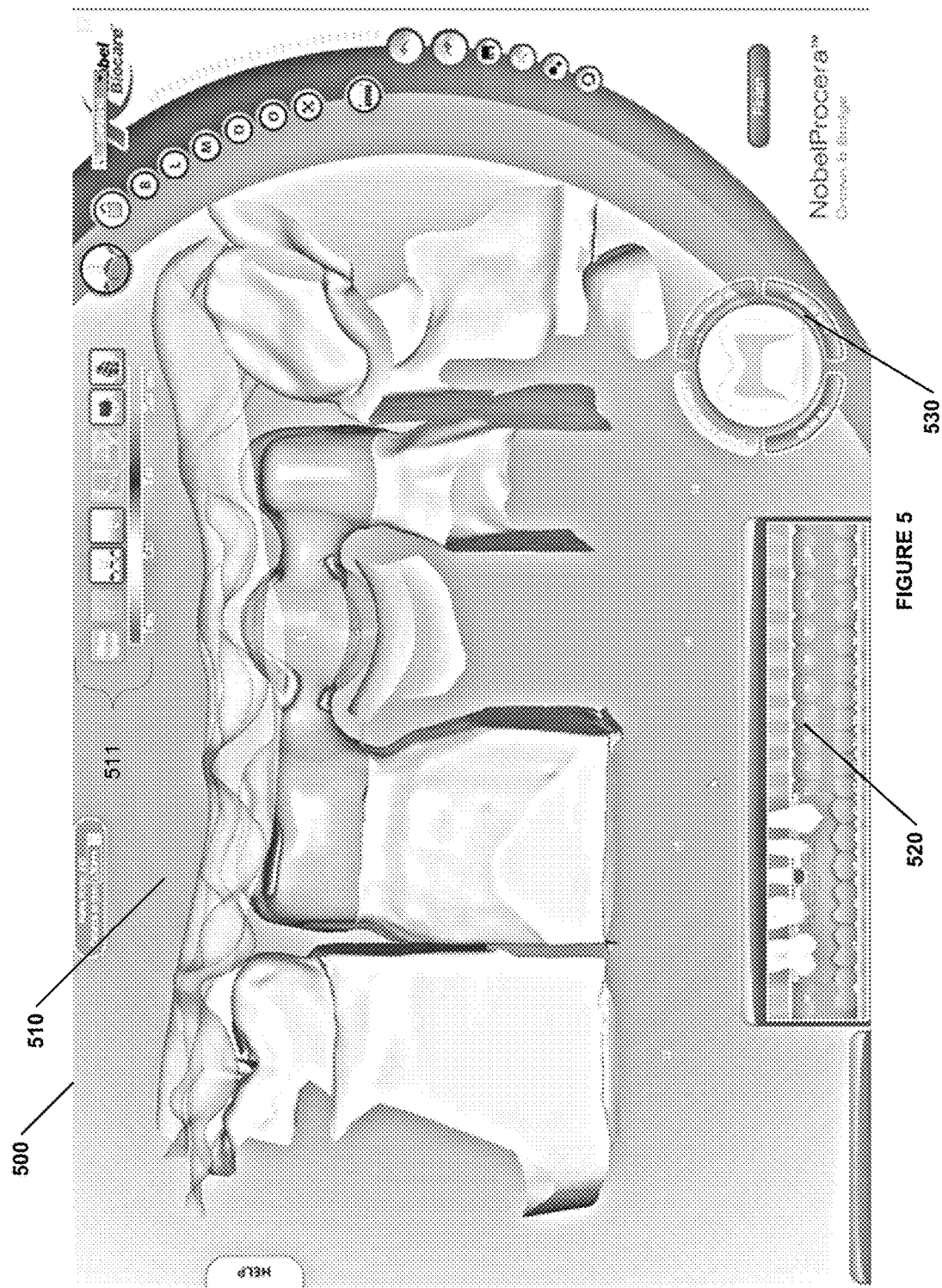
FIG. 5 illustrates a third display for dental prosthetics, manipulation, selection, and planning.

Perhaps in concert with or sequentially before or after the overlapped representation is presented in the first display in step 320, in step 330, one or more abstract representations are presented in a display. For example, turning to FIG. 4, which illustrates a another embodiment of a display 400 for dental prosthetics, manipulation, selection, and planning, an expanded tooth setup could be displayed in a localized abstraction portion 420. The expanded tooth setup may show a cross-section of all or various tooth positions in a human mouth in a non-overlapped fashion, including the various components of the patient-specific data and the dental plan in a non-overlapping manner. In some embodiments, a globalized abstraction of the dental data may be displayed in the globalized abstraction portion 430 of FIG. 4. A representation of the dental data may be displayed in either or both of the portions 420 and 430. In FIG. 5, a localized tooth setup is shown in portion 520 and a globalized abstraction of the dental data is displayed in portion 530. Either or both of the localized abstraction portion 520 and globalized abstraction portion 530 may be shown.

An operator may issue commands via the computer system (such as by interacting with the localized, globalized, and/or overlapped portions of the display) and these commands may be received in step 340. Various commands are discussed more herein and with respect to FIG. 1, but, in addition to the manipulation of the dental data discussed above and elsewhere herein, some of the received commands may include making a particular portion of the dental data transparent or invisible; selection of a portion of the plan; etc. Once the commands are received, then in step 350, the operations associated with the received commands are represented in at least portion 410. For example, consider FIG. 1. If the operator right-clicks on the crown in the global abstract portion 130, then the overlapped portion 110 may be updated to make all of the crowns in the dental plan transparent. In some embodiments, the crowns may be made transparent or otherwise indicated as transparent (e.g., by re-coloring the crowns in the abstract displays).

As noted throughout, the existence of a localized abstraction portion and/or a globalized abstraction portion may allow an operator to more easily perform various commands on the data. These commands may include selections or other manipulations (e.g., Make Visible or Make Invisible) either on an individual-tooth level in the localized abstraction portion of the screen or on a global, all-tooth positions level in the globalized abstraction portion. Both the localized and globalized portions provide a way for the operator to select or manipulate aspects of the dental data in a non-overlapped environment, which may not be possible in the overlapped portion of the display.

Example Selections, Manipulations, and Interactions

Figure 12:
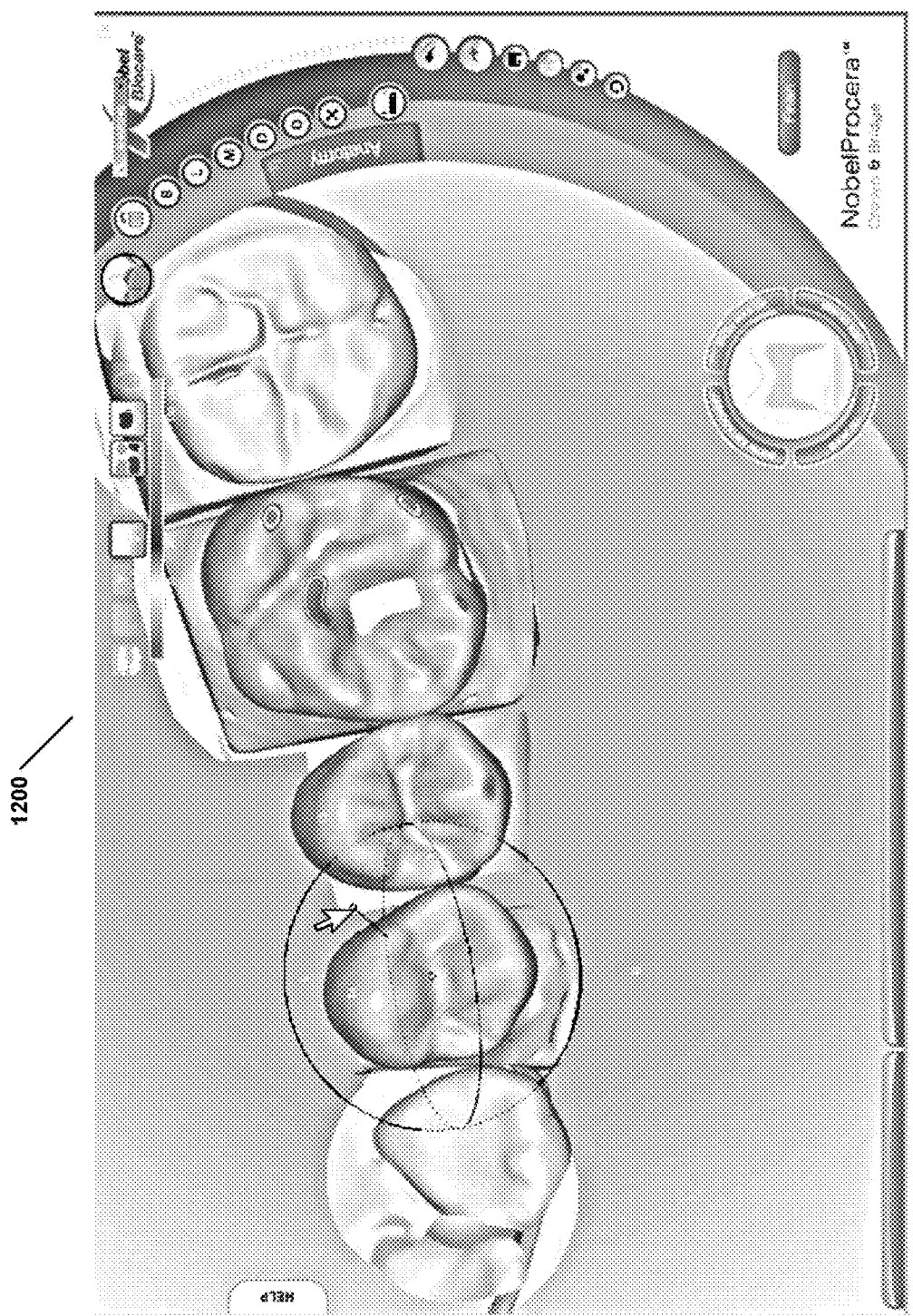
FIG. 12 illustrates a tenth display for dental prosthetics, manipulation, selection, and planning.
Figure 13:
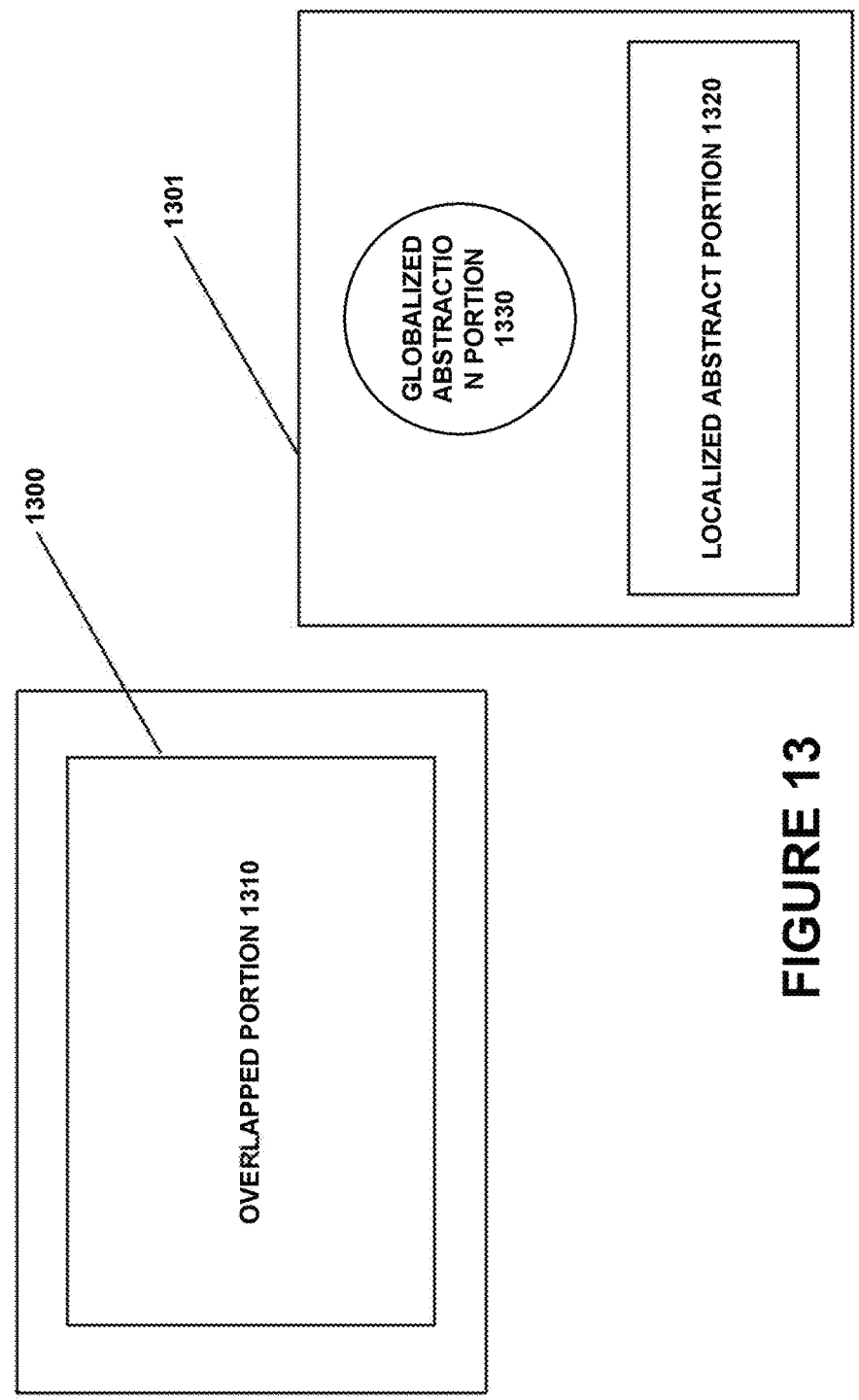
FIG. 13 illustrates an eleventh display for dental prosthetics, manipulation, selection, and planning.

The discussion above and herein provides an overview of embodiments of the systems, processes, and methods for dental planning. Following is a discussion of exemplary embodiments with various interactions in dental prosthetics, manipulation, selection, and planning. FIGS. 1, 4-12 are illustrations of various displays for dental prosthetics, manipulation, selection, and planning. Each of these displays may be generated by one or more computer systems 210 and displayed on one or more display 220, both of FIG. 2. In the example displays of FIGS. 1, 4-12, the display and/or manipulation of dental data related to abutments, crowns, bars, and bridges are variously shown. Numerous other systems and types of dental plans are also possible. For example, various embodiments can also be used for copings, pontics, and other dental designs. Additionally, the displays of FIGS. 1, 4-12 may be interpreted to depict multiple portions, displays (or sub-displays) on a single screen. The embodiments herein are not so limited, however. Various portions may be displayed on multiple displays. As depicted in FIG. 13, an overlapped portion 1310 may be on a first display 1300 and one or more abstract portions 1320 and 1330 may be on a second display 1301.

Globalized Abstraction

Figure 7:
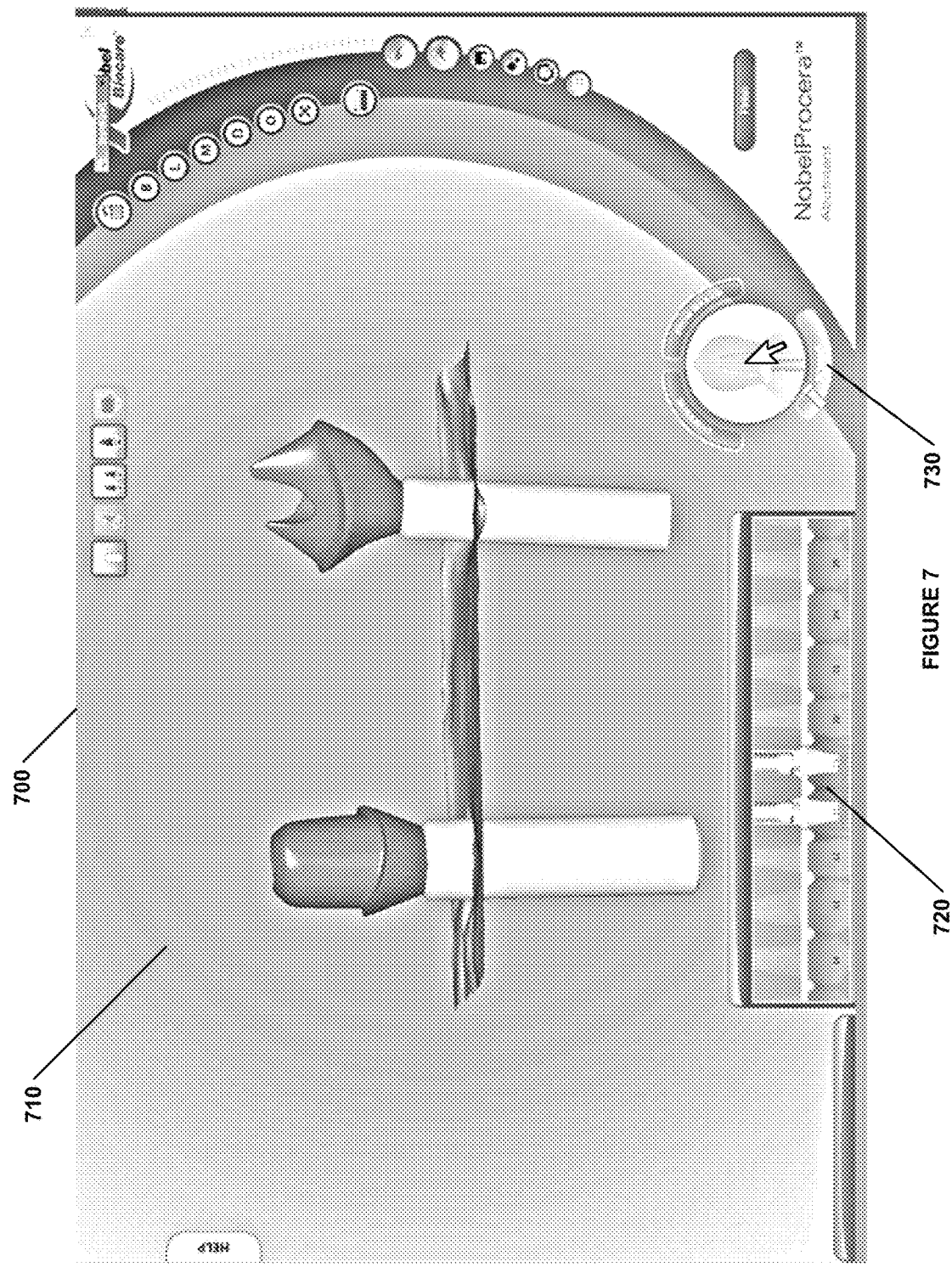
FIG. 7 illustrates a fifth display for dental prosthetics, manipulation, selection, and planning.
Figure 14:
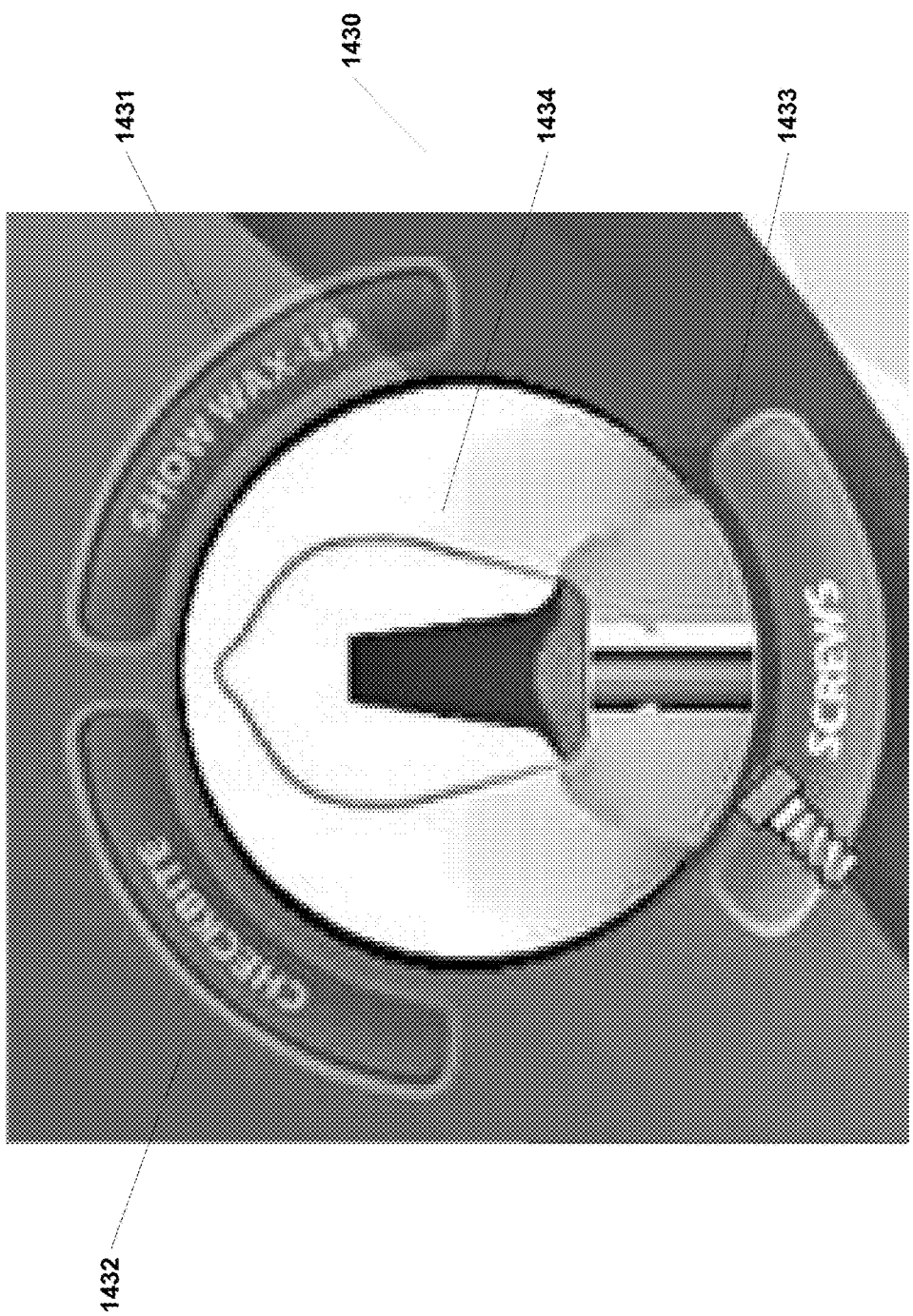
FIG. 14 illustrates an expanded view of a portion of a display for dental prosthetics, manipulation, selection, and planning.

FIG. 7 shows a display 700, which includes a globalized abstraction portion 730, which includes a number of abstractions of a general dental plan. FIG. 14 is a larger version of a globalized abstraction portion 1430 similar to portion 730. The abstractions included may include various aspects of an exemplary tooth or preparation, such as bone, gum line, implant, abutment, coping, crown, etc. The exemplary abstraction tooth may also include the various aspects of bridge design, crown design, etc. This is shown in detail in the abstract tooth portion 1434 of globalized abstraction portion 1430 in FIG. 14. When a particular aspect of the abstract tooth in portion 1434 is selected, for example, that particular aspect is selected for all teeth in the dental data, which may include single or multiple teeth or units. The globalized abstraction portion 1430 may enable numerous types of global interaction with all of the teeth, units, etc. in the plan or data. Interacting with this globalized abstraction portion 730, an operator may be able to perform an operation on all of the tooth positions or units in the plan. For example, as pictured, an operator is interacting with the abutment portion of the global plan. When the operator left-clicks (on a two button mouse, e.g.) on the abutment of the abstract tooth in portion 1434, all of the abutments for each tooth position in the dental data may be made visible in an accompanying overlapped portion (not pictured in FIG. 14, but may be similar to portion 710 in FIG. 7). An operator may be able to perform other operations in the globalized abstraction portion by right-clicking (in order to make invisible), double-clicking (in order to make transparent), dragging a clicked mouse (in order to alter transparency), or hitting keystrokes (in order to manipulate the visibility in some way). FIG. 1, for example, depicts the result of making the crowns appear transparent from the globalized abstraction portion 130, which is reflected in the overlapped portion 110.

Returning to FIG. 7, in some embodiments, an indication of the visibility of the abutments may also be made in the localized abstraction display 720 based upon action in the globalized portion of the display 730. This indication in the localized abstraction portion 720 may be a color or the abutments (or other aspects of the dental data) may be made visible or may be filled in (as opposed to remain in outline). In some embodiments, components remain visible in the localized abstraction portion 720 regardless of whether they are visible or invisible in the overlapped portion 710.

Returning again to FIG. 14, in some embodiments, the globalized abstraction portion 1430 includes one or more buttons that allow manipulation of the dental data. For example, in the case of an implant-supposed restoration, you may want to see the restoration holes that will attach the prosthesis to the implant. The globalized abstraction portion 1430 may have a Screws button 1433 that, when clicked, toggles between two states: having screws being displayed and having screws removed or invisible in the overlapped portion. In some embodiments, the screws may recede when removed or may become invisible. Similarly, the screws may "fly in" or simply appear when they are again displayed. Other examples buttons are a Checkbite button 1432 and a Show Antagonist button (not pictured in FIG. 14). When pressed, these buttons may show or make invisible an indication of opposing teeth, such as a checkbite for the dental plan. A visible checkbite is shown in the overlapped portion 510 of FIG. 5.

Figure 8:
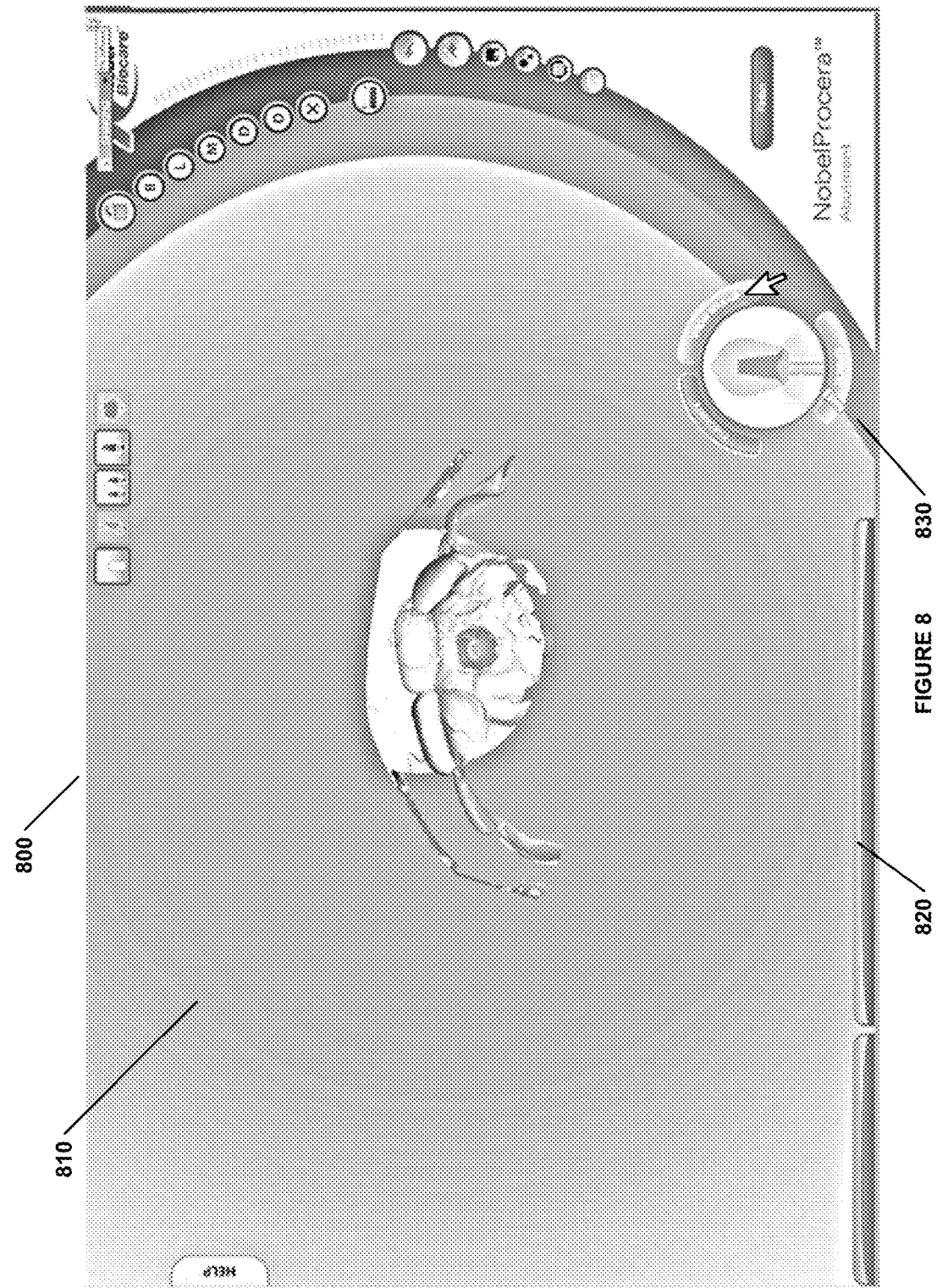
FIG. 8 illustrates a sixth display for dental prosthetics, manipulation, selection, and planning.

In some embodiments, clicking on the Show Antagonist button toggles the checkbite in the overlapped portion 710 (or 510) among multiple states, such as: visible, one or more transparency states, and invisible. Another example button that may be available for the operator in the globalized abstraction portion 1430 is a Show Wax-Up button 1431. When pressed, this button may toggle the display of a wax up in the accompanying overlapped portion among two or more states, such as: visible, invisible, and transparent. The clicking of this button in a globalized abstraction portion 830 is depicted in FIG. 8, which illustrates another embodiment 800 of a display for dental prosthetics, manipulation, selection, and planning. After clicking the Show Wax-Up button, the wax-up is visible in overlapped portion 810. Also depicted in FIG. 8 is that one or more of the display portions can be minimized or removed. Localized abstraction portion 820 has been minimized in FIG. 8. In some embodiments, other buttons may be added to the globalized abstraction portions 730, 830, and/or 1430, including a button to make the entire plan visible, invisible, or transparent. Additionally, one or more additional operations may be performed on the globalized abstraction portion. For example, an operation might make invisible all but the selected item (e.g., triple clicking on the crown might make all of the crowns visible and the rest of the plan invisible).

The operations available in a globalized abstraction portion may also vary based on the type of dental plan or data. The dental plan in FIG. 7 may be for the design of two abutments and, optionally, related dental prostheses. FIG. 5, on the other hand, may represent the design of a bridge. The globalized abstraction portion 530 depicts a set of operations that may be operable on dental data related to bridge design and the operations may be reflected in the overlapped portion 510 and/or the localized abstraction portion 520. Clicking on the various portions of the globalized abstraction in the globalized abstraction portion 530 may make visible (e.g., by a left click of a mouse), make invisible (e.g., by a right click of a mouse), or make transparent (e.g., by a double-click of a mouse). As noted above, numerous other operations may also be available. Double-clicking on the coping portion of the globalized abstraction portion 530 may make the coping transparent in overlapped portion 510. Additional buttons that may be available in the globalized abstraction portion 530 include the Show Antagonist, which may toggle among states (e.g., invisible and transparent), Show All (which may display all aspects of every tooth position), and Hide Others (which may hide all but the selected tooth positions or units—those units having been selected in either the localized abstraction portion 520 or the overlapped portion 510).

Localized Abstraction

Figure 15:
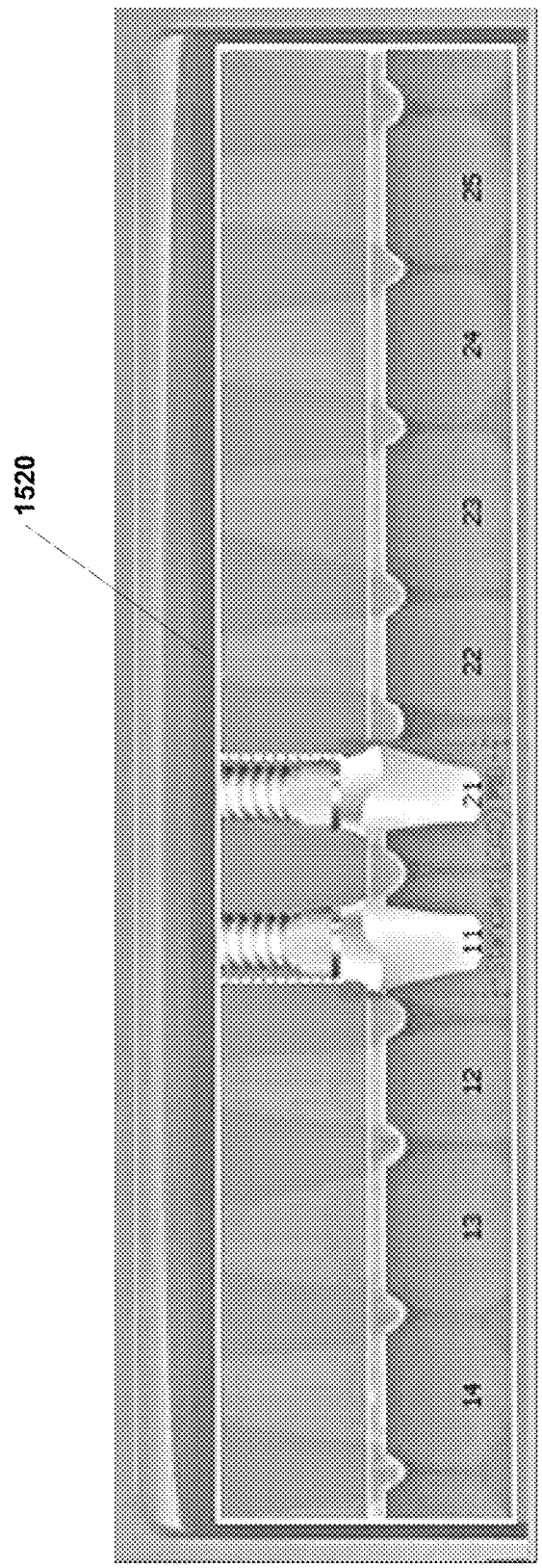
FIG. 15 illustrates an expanded view of a portion of a display for dental prosthetics, manipulation, selection, and planning.

Returning again to FIG. 7, the localized abstraction portion 720 may be used to perform operations on single or multiple tooth positions or units. An enlarged localized abstraction portion 1520 is depicted in FIG. 15. Similar to the case for the globalized abstractions, the abstractions included in the localized portion of the display may include various aspects of an exemplary tooth or preparation, such as bone, gum line, implant, abutment, coping, crown, etc. The localized abstraction may also include the various aspects of bridge design, crown design, etc. The localized abstraction may be a cross-section of the dental data. The localized abstraction may provide a non-overlapped view of all aspects of the dental data, and thereby allow interaction with the dental data (such as selection or manipulation) that would not be possible in an overlapped portion of the display because of the overlapped nature of an overlapped data display.

Localized abstraction portion 1520 depicts the abstraction of a dental plan for two teeth. An operator may be able to select individual portions of the dental data by selecting that (or those) portions in the localized abstraction portion 1520. For example, consider FIG. 1, if an operator selects the localized abstraction of a particular tooth position's abutment in portion 120, then that selection may be reflected in the overlapped portion 110. In some embodiments, an operator may also be able to select the abutment in the overlapped portion 110, but, as discussed herein, a problem may occur if the operator attempts to select the abutment where it is overlapped with the semi-transparent crown. It may be difficult for the system to determine if the operator is attempting to select the semi-transparent crown or the underlying abutment in the overlapped portion 110. Since the abstraction in localized abstraction portion 120 is not overlapped in the same way, it may be possible to select, in the localized abstraction portion 120, aspects of dental data that overlap other aspects of the dental data when displayed in the overlapped portion 110.

Returning again to FIG. 7, and similar to the case for the globalized abstraction portion 730, in some embodiments, numerous operations may be performable by interacting with the localized abstraction portion 720. For example, left-clicking a mouse may make the selected object visible, right-clicking a mouse may make the object invisible; double-clicking may make the object semi-transparent, etc. Numerous other examples and embodiments of operations may apply as well.

Figure 9:
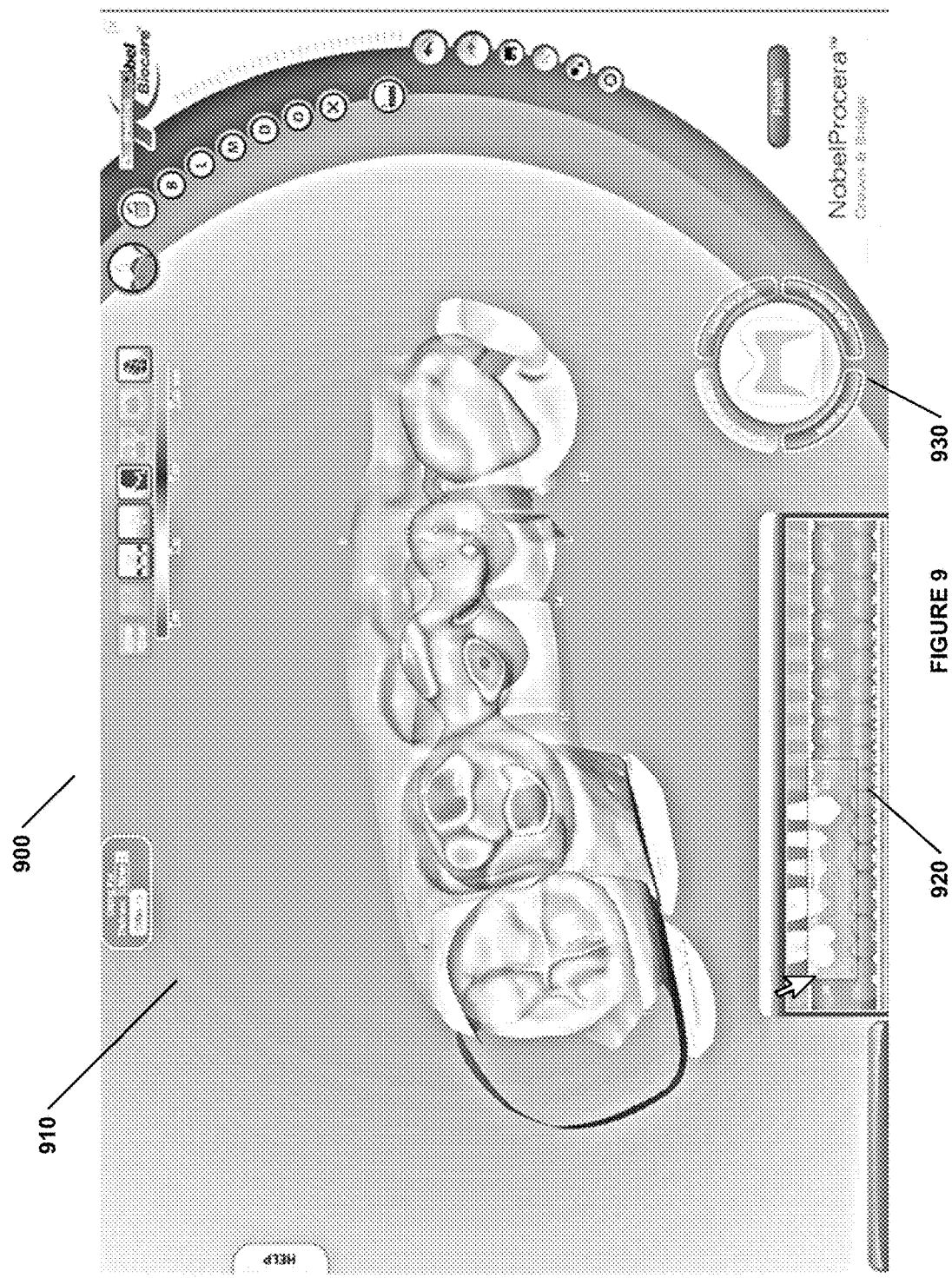
FIG. 9 illustrates a seventh display for dental prosthetics, manipulation, selection, and planning.

As depicted in FIG. 9, which illustrates another embodiment of a display 900 for dental prosthetics, manipulation, selection, and planning, in various embodiments, an operator may be able to perform an operation on multiple aspects of a tooth position and/or one or more aspects of multiple tooth positions in a single operation by clicking and dragging a region, such as a rectangle, across the localized abstraction portion 920. In some embodiments, the operation performed on the multiple tooth positions or multiple portions of tooth positions may be selection, make invisible, make visible, make semi-transparent, or any other operation. For example, an operator might select multiple units or teeth in dental data in localized abstraction portion 920 and then select the Hide Others button in the globalized abstraction portion 930. This may have the effect of hiding everything else in the overlapped portion except those tooth positions selected in the localized abstraction portion 920. Additionally, if an operator performed a Make Invisible operation on all of the tooth positions and then selected a few of the tooth positions for display, both in the localized abstraction portion 920, then only those tooth positions may be displayed in the overlapped portion 910.

Overlapped Display

Returning again to FIG. 7, the overlapped portion 710 may show the dental data. In some embodiments, the dental data is rendered in 3D, shown in a semi-realistic manner, or otherwise displayed in a manner that is understandable to an operator. For example, the 3D rendering may be based on polygons or voxels, and the surfaces may be reflective or matte. In some embodiments, other rendering techniques are used, such as mesh display, simulated drawing (e.g., in black and white pencil or pen), or using any other technique known to those skilled in the art. The point of view of the overlapped portion 710 may be rotated using click-and-drag motions of the mouse, keystrokes, or using viewing buttons on the overlapped portion. FIG. 9, for example, depicts buttons, that when selected, can change the viewing direction to lingual ("L"), occlusal ("O"), and other views. An operator may be able to press one of the buttons to the right of the overlapped portion 910 and the overlapped portion may be shown from a certain predefined viewpoint (note the "L" and "O" in the overlapped portion showing the general position of the viewpoint once the "L" or "O" buttons are pressed).

Figure 10:
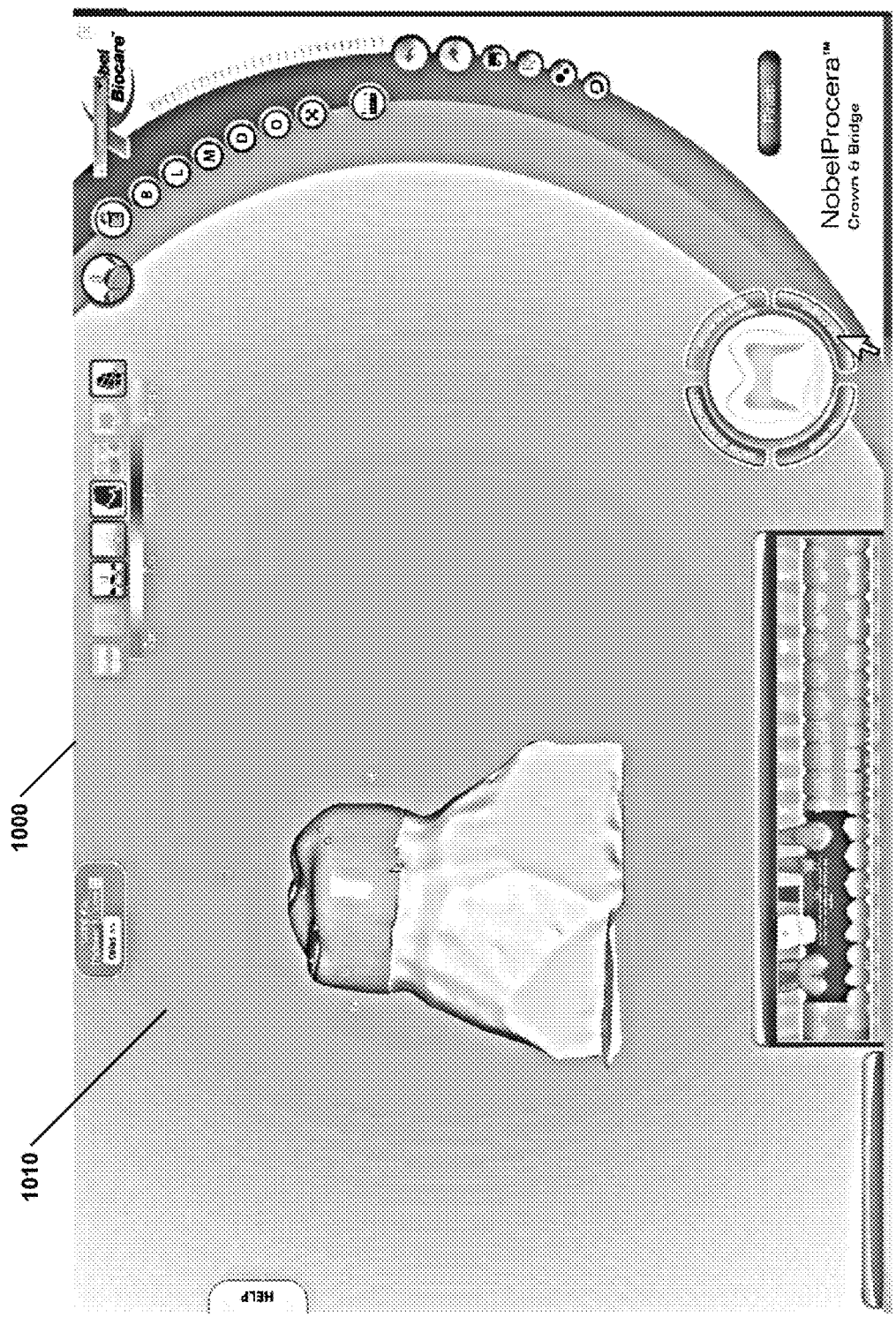
FIG. 10 illustrates an eight display for dental prosthetics, manipulation, selection, and planning.

Considering now FIG. 5, and as discussed above, an operator may be able to select a portion of the dental data in the overlapped portion 510 (or do so in the localized abstraction portion 520). If the operator selected the crown of one of the tooth positions and then clicked on the Hide Others button (not depicted), then, as illustrated in FIG. 10, which illustrates another embodiment of a display 1000 for dental prosthetics, manipulation, selection, and planning, the data for the single tooth position may be displayed in the overlapped portion 1010. In some embodiments, if the operator selects a certain aspect of the data for the tooth position, such as the crown or abutment, then everything "below" the selection portion may be displayed. The display may include all of the aspects that are apically positioned (e.g., towards the root) or coronally positioned (towards the crown). In some embodiments, only the selected portion remains visible when the Hide Others button is pressed. There are similar embodiments in which the operator is planning a coping for one or more tooth positions. The operator may be able to select the coping in the localized abstraction portion, click the Hide Others button in the globalized abstraction portion, and plan the coping in the overlapped portion.

In some embodiments, an overlapped portion may also provide useful information via shade or colors. Consider, for example, FIG. 5. In some embodiments, in the overlapped portion 510, the distance to the antagonist is shown in shades. These shades are depicted in FIG. 5 in the overlapped portion 510. In various embodiments, the distance may also be shown in color, with, for example, red being the closest and green being the furthest. In some embodiments, overlapped portion also has a legend, as depicted in overlapped portion 510, that shows that to which the various colors correspond. In some embodiments, a display 500 may also have a button that toggles between coloring modes. For example, there may be two shade or color modes: an inward-facing and an outward-facing mode. The one described above may be an outward-facing mode because it depicts in shades or color the distance out to the antagonistic teeth. In some embodiments, inward facing mode may show thickness of layers (such as abutments, copings, crowns, etc) or distance to inner surfaces. These shades or colors may provide useful information to operators because there may be standard or desired distances or thicknesses. For example, for certain materials, it may be desirable that a portion of the bridge be a certain distance from the antagonistic teeth in order to allow for an appropriate cover for that portion and maintain a proper bite. Coloring the bridge with distances may provide a quick way for an operator to determine that the bridge is too tall or too close and modify it appropriately.

Dental Data Manipulation

Figure 6:
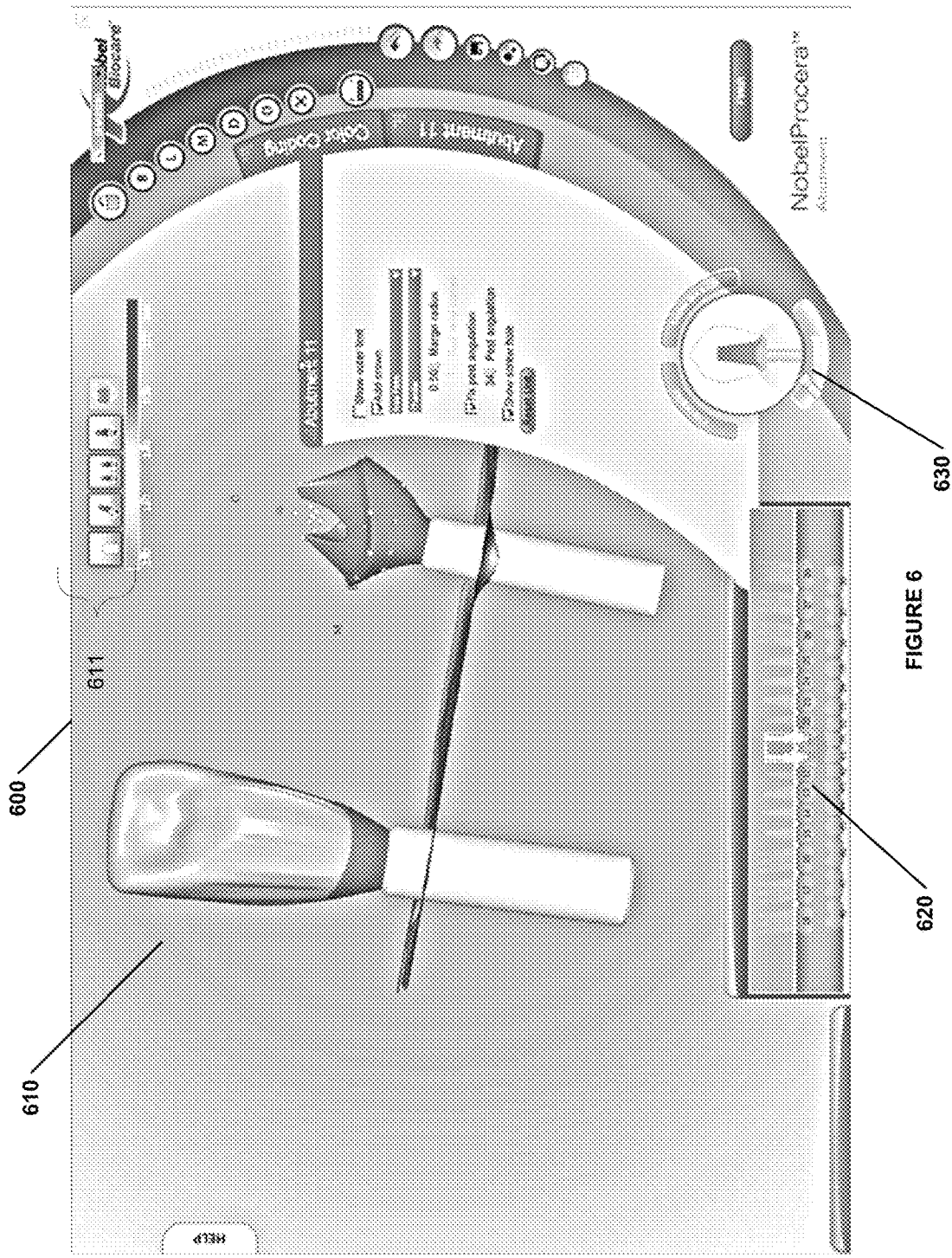
FIG. 6 illustrates a fourth display for dental prosthetics, manipulation, selection, and planning.

In addition to the selection and control of visibility of various aspects of the dental plans, and referring again to FIG. 6, the elements of display 600 may be used to manipulate the dental data. In some embodiments, for example, the overlapped portion 610, possibly in concert with the abstract portions 620 and 630, may be used by an operator to reshape a crown or abutment or manipulate the placement, pose, or location or one or more of the aspects of the dental plan. As depicted in FIG. 6, the overlapped portion may include an Abutment button or tab that, when selected, opens a menu that allows the operator to show the outer limits of the unit, add a standard or predefined crown, modify that crown, fix and modify the post angulation, toggle whether the screw hole is depicted, and/or reset the unit. There may be one such button or tab and menu for each tooth position or a global one for all tooth positions.

As also depicted in FIG. 6, various aspects of dental data may be manipulated in the overlapped portion 610. As depicted, the abutment of a tooth position has been selected and various surface and angulation points are displayed. An operator may be able to manipulate those points in order to reshape and/or rotate the abutment. The same may be true for other portions of the dental data, such as the crown or the implant. Turning to FIG. 5, similar manipulations may be available for bridges. An operator may be able to manipulate the size, shape, and position of a bridge by moving points or controls on the bridge in the overlapped portion 510 (not pictured).

Figure 11:
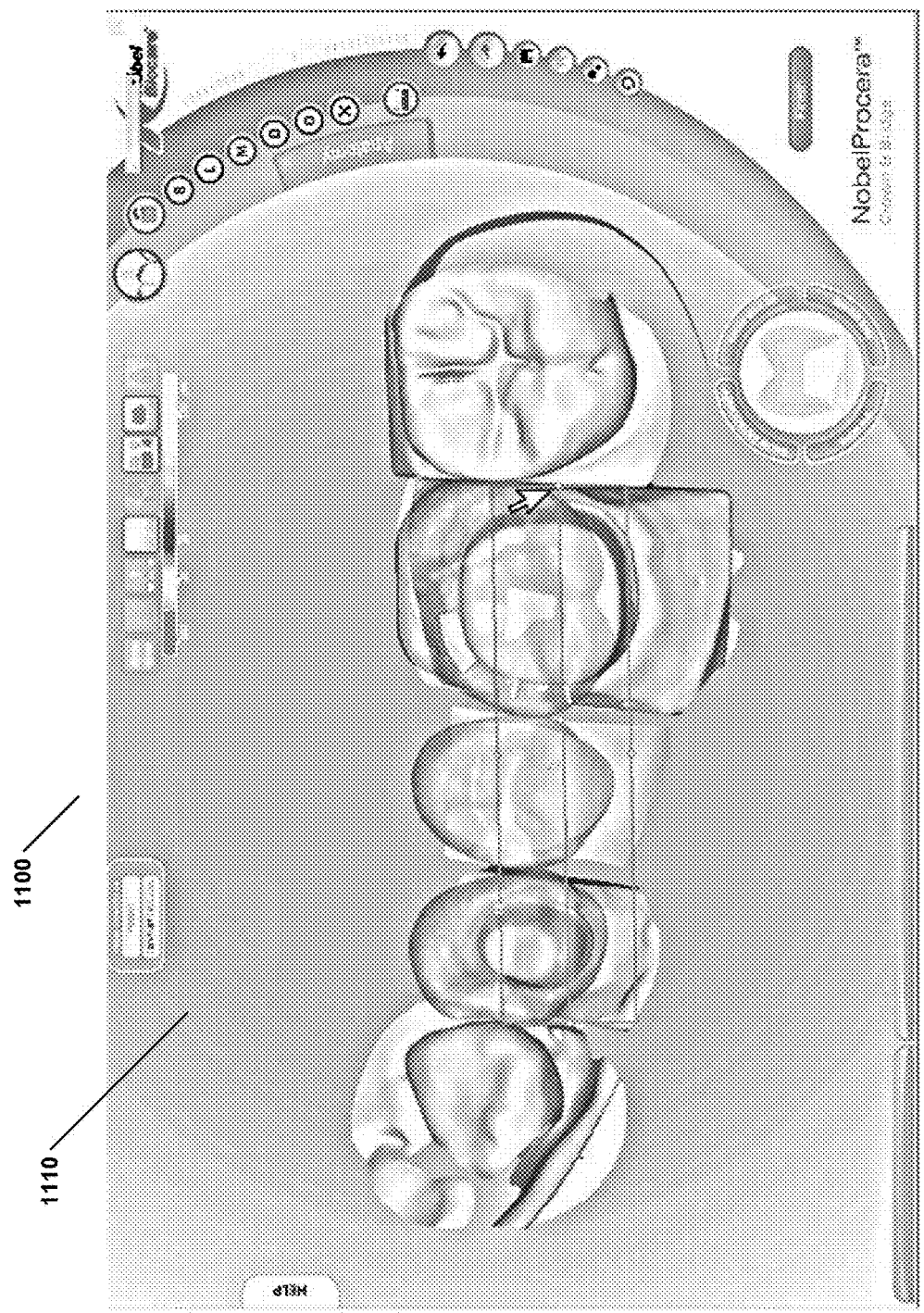
FIG. 11 illustrates a ninth display for dental prosthetics, manipulation, selection, and planning.

FIG. 11 illustrates another embodiment of a display 1100 for dental prosthetics, manipulation, selection, and planning that depicts another example of manipulation of a bridge. In some cases, it is important for the buccal cusps in a bridge to be aligned. The buccal cusps may be aligned when the bridge is initially placed because they are aligned in the scanned gypsum model or in the standard bridge library from which the bridge is selected. An operator may also align the buccal cusps manually. In some embodiments, an operator may modify units in a bridge individually (as depicted in FIG. 12, which illustrates another embodiment of a display 1200 for dental prosthetics, manipulation, selection, and planning). This individual alignment may cause the buccal cusps to become misaligned.

Returning to FIG. 11, in some embodiments, using a bridge manipulation tool, such as that depicted in the overlapped portion 1110, the operator may be able to grow, shrink, rotate, skew, displace, etc., the bridge as a whole. This whole-bridge manipulation may allow an operator to manipulate the bridge so that it fits within the allowed envelope and still maintains the alignment of a buccal cusp. This may also be accomplishable using the single-tooth position manipulation of FIG. 12, but it may be accomplished more easily using a global bridge manipulation tool.

Design Stages

A display may also include two or more buttons or icons that depict and guide an operator through various aspects of designing a dental plan. Consider, for example, FIG. 5, which has eight buttons 511 that depict various stages of dental plan manipulation for bridges. These stages may include impression matching, impression preparation and cutting, bridge insertion axis definition, orientation, margin line definition, global crown and arch placement, individual crown placement, and local deformation tool. Turning to FIG. 6, there are five example buttons 611 that depict various stages of abutment design, including implant alignment, abutment orientation, parallel abutments, color coding tool, and crown manipulation. In some embodiments, fewer than these numbers of buttons are used and in other embodiments, more than this number of buttons are used. The buttons may be useful in guiding an operator through the steps needed to design a dental plan, such as an abutment or a bridge, and may also provide a quick link to another design stage of a dental plan. Additionally, in some embodiments, each of these buttons may be associated with various viewing parameters. For example, for an abutment orientation button, there may be a default viewing from the lingual direction with the abutment and implant visible and any associated crown invisible.

The processes, computer readable medium, and systems described herein may be performed on various types of hardware, such as computer systems. In computer systems may include a bus or other communication mechanism for communicating information, and a processor coupled with the bus for processing information. A computer system may have a main memory, such as a random access memory or other dynamic storage device, coupled to the bus. The main memory may be used to store instructions and temporary variables. The computer system may also include a read-only memory or other static storage device coupled to the bus for storing static information and instructions. The computer system may also be coupled to a display, such as a CRT or LCD monitor. Input devices may also be coupled to the computer system. These input devices may include a mouse, a trackball, or cursor direction keys. Computer systems described herein may include the computer 210, display 220, and/or input device 230. Each computer system may be implemented using one or more physical computers or computer systems or portions thereof. The instructions executed by the computer system may also be read in from a computer-readable medium. The computer-readable medium may be a CD, DVD, optical or magnetic disk, laserdisc, carrier wave, or any other medium that is readable by the computer system. In some embodiments, hardwired circuitry may be used in place of or in combination with software instructions executed by the processor.

As will be apparent, the features and attributes of the specific embodiments disclosed above may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and fully automated via, software code modules executed by one or more general purpose computers or processors, such as those computer systems described above. The code modules may be stored in any type of computer-readable medium or other computer storage device. Some or all of the methods may alternatively be embodied in specialized computer hardware.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A method for dental prosthetics manipulation, selection, and planning, comprising:
   receiving, from an operator via a computer system, dental data related to a desired dental plan for one or more tooth positions;
   presenting to the operator, using the computer system, an overlapped electronic representation of two or more aspects of the dental data;
   providing to the operator a graphical user interface for manipulating a representation of one of said two or more aspects of said overlapped electronic representation, using the computer system, said graphical user interface presenting a non-overlapped abstract electronic representation of the two or more aspects of the dental data, wherein the non-overlapped abstract electronic representation comprises a single globalized unit representation of the one or more tooth positions;

through said graphical user interface, receiving at the computer system, relative to the single globalized unit representation of the one or more tooth positions, an indication of an operation to be performed regarding one of the two or more aspects of the dental data; and presenting, in the overlapped electronic representation, said operation, whereby said one aspect is manipulated for each of the one or more tooth positions, wherein said operation is selected from the group consisting of make transparent, make visible, and make invisible.

2. The method of claim 1, wherein the one of the two or more aspects is selected from the group consisting bone, gum line, implant, abutment, coping, bridge, screw, checkbite, opposing teeth, and wax-up.

3. The method of claim 1, wherein make transparent is performed by double-clicking, make visible is performed by left-clicking, and make invisible is performed by right-clicking, on a computer mouse.

4. The method of claim 1, wherein:
the dental data comprises a dental plan for two or more teeth; wherein the non-overlapped abstract electronic representation of the two or more aspects of the dental data comprises a localized abstract electronic representation of each tooth in the dental plan; and wherein the method further comprises:
receiving at the computer system, relative to the localized abstract electronic representation of the non-overlapped abstract electronic representation, a selection of at least one of said two or more teeth; and
presenting, in the overlapped electronic representation, an operation indicated for the at least one tooth of said selection.

5. The method of claim 1, further comprising using said non-overlapped abstract electronic representation to select or manipulate a plurality of like aspects of the dental data all at once.

6. The method of claim 1, further comprising using said single globalized unit representation of the one or more tooth positions to select or manipulate a plurality of like aspects of the dental data all at once.

7. The method of claim 1, wherein the overlapped electronic representation is presented on a first sub-display portion of a screen and the single globalized unit representation is presented on a second sub-display portion of the screen.

8. The method of claim 1, wherein the overlapped electronic representation is presented on a first screen and the single globalized unit representation is presented on a second screen.

9. A computer system for dental prosthetics manipulation, selection, and planning, the computer system configured to:
receive, from an operator via the computer system, dental data related to a desired dental plan for one or more tooth positions;
present, on an electronic display, to the operator an overlapped electronic representation of two or more aspects of the dental data;
provide, on the electronic display, to the operator a graphical user interface for manipulating a representation of one of said two or more aspects of said overlapped electronic representation, said graphical user interface presenting a non-overlapped abstract electronic representation of the two or more aspects of the dental data, wherein the non-overlapped abstract electronic representation comprises a single globalized unit representation of the one or more tooth positions;
receive at the computer system through said graphical user interface, relative to the single globalized unit representation of the one or more tooth positions, an indication of an operation to be performed regarding one of the two or more aspects of the dental data; and
present, on the electronic display, in the overlapped electronic representation, said operation, whereby said one aspect is manipulated for each of the one or more tooth positions and wherein said operation is selected from the group consisting of make transparent, make visible, and make invisible.

10. The system of claim 9, wherein the one of the two or more aspects of the dental data are selected from the group consisting of bone, gum line, implant, abutment, coping, bridge, screw, checkbite, opposing teeth, and wax-up.

11. The system of claim 9, wherein said make transparent is performed by double-clicking, make visible is performed by left-clicking, and make invisible is performed by right-clicking, on a computer mouse.

12. The system of claim 9, wherein:
the dental data comprises a dental plan for two or more teeth; wherein the non-overlapped abstract electronic representation of the two or more aspects of the dental data comprises a localized abstract electronic representation of each tooth in the dental plan; and wherein the computer system is further configured to:
receive at the computer system, relative to the localized abstract electronic representation of each tooth in the dental plan of the non-overlapped abstract electronic representation, a selection of at least one of said two or more teeth; and
present, in the overlapped electronic representation, an operation indicated for the at least one tooth of said selection.

13. The method of claim 9, wherein the computer system is further configured to use said non-overlapped abstract electronic representation to select or manipulate a plurality of like aspects of the dental data all at once.

14. The method of claim 9, wherein the computer system is further configured to use said single globalized unit representation of the one or more tooth positions to select or manipulate a plurality of like aspects of the dental data all at once.

15. A method for dental prosthetics manipulation, selection, and planning, comprising:
receiving, from an operator via a computer system, dental data related to a desired dental plan;
presenting to the operator, using the computer system, an overlapped electronic representation of two or more aspects of the dental data;
providing to the operator a graphical user interface for manipulating a representation of one of said two or more aspects of said overlapped electronic representation, using the computer system, said graphical user interface presenting a non-overlapped globalized abstract electronic representation of the two or more aspects of the dental data;
through said graphical user interface, receiving at the computer system, relative to the non-overlapped globalized abstract electronic representation, an indication of an operation to be performed regarding a particular aspect of the two or more aspects of the dental data; and presenting, in the overlapped electronic representation, said operation regarding the particular aspect, the operation being presented for all teeth in the dental data wherein said operation is selected from the group consisting of make transparent, make visible, and make invisible.

16. The method of claim 15, wherein said operation that is selected from the group consisting of make transparent, make visible, and make invisible makes transparent, visible, and or invisible a portion of the overlapped electronic representation of two or more aspects of the dental data.

17. The method of claim 15, further comprising using said non-overlapped abstract globalized abstract electronic representation to select or manipulate a plurality of like aspects of the dental data all at once.

* * * * *